(12) United States Patent
Carr et al.

(10) Patent No.: US 9,217,054 B2
(45) Date of Patent: *Dec. 22, 2015

(54) PROCESS FOR PRODUCTION OF DI- AND POLYAMINES OF THE DIPHENYLMETHANE SERIES

(75) Inventors: Robert Carr, Bertem (BE); Johannes Lodewijk Koole, Kessel-lo (BE); Willem Van Der Borden, Rotterdam (NL)

(73) Assignee: Huntsman International LLC, The Woodlands, TX (US)

( * ) Notice: Subject to any disclaimer, the term of this patent is extended or adjusted under 35 U.S.C. 154(b) by 383 days.

This patent is subject to a terminal disclaimer.

(21) Appl. No.: 12/677,851

(22) PCT Filed: Aug. 28, 2008

(86) PCT No.: PCT/EP2008/061349
§ 371 (c)(1),
(2), (4) Date: Apr. 22, 2010

(87) PCT Pub. No.: WO2009/037087
PCT Pub. Date: Mar. 26, 2009

(65) Prior Publication Data
US 2011/0263809 A1    Oct. 27, 2011

(30) Foreign Application Priority Data
Sep. 19, 2007   (EP) ..................... 07116764

(51) Int. Cl.
*C08G 12/08*   (2006.01)
*C08G 18/00*   (2006.01)
*C07C 209/78*  (2006.01)
*C08G 73/02*   (2006.01)
*C08G 12/00*   (2006.01)
*C08G 12/02*   (2006.01)

(52) U.S. Cl.
CPC .............. *C08G 12/08* (2013.01); *C07C 209/78* (2013.01); *C08G 73/0266* (2013.01)

(58) Field of Classification Search
CPC ...................................... C08G 12/08
USPC ................. 528/239, 489, 491, 499, 500, 501, 528/502 R, 502 D, 503, 243, 482
See application file for complete search history.

(56) References Cited

U.S. PATENT DOCUMENTS

| | | |
|---|---|---|
| 3,362,979 A | 1/1968 | Bentley |
| 3,478,099 A | 11/1969 | Ross et al. |
| 3,676,497 A | 7/1972 | Recchia et al. |
| 3,996,283 A | 12/1976 | Knofel |
| 4,039,580 A | 8/1977 | Frulla et al. |
| 4,039,581 A | 8/1977 | Frulla et al. |
| 4,067,805 A | 1/1978 | Chiang et al. |
| 4,094,907 A | 6/1978 | Knöfel et al. |
| 4,130,588 A | 12/1978 | Martin et al. |
| 4,250,114 A | 2/1981 | Biller |
| 4,297,294 A | 10/1981 | Mango |
| 4,798,909 A | 1/1989 | Biller |
| 5,196,591 A | 3/1993 | Knöfel et al. |
| 5,359,141 A | 10/1994 | Knöfel et al. |
| 5,679,841 A | 10/1997 | Knöfel et al. |
| 5,684,180 A | 11/1997 | Knöfel et al. |
| 6,031,136 A | 2/2000 | Renbaum et al. |
| 6,610,888 B1 | 8/2003 | Strofer et al. |
| 6,673,970 B1 | 1/2004 | Renbaum et al. |
| 7,582,638 B2 | 9/2009 | De Dios et al. |
| 7,943,724 B2 * | 5/2011 | Carr .............................. 528/269 |
| 2003/0045745 A1 | 3/2003 | Hagen et al. |
| 2006/0094897 A1 | 5/2006 | Muller et al. |
| 2006/0287555 A1 | 12/2006 | Hagen et al. |
| 2007/0179317 A1 | 8/2007 | Keggenhoff et al. |
| 2008/0312405 A1 | 12/2008 | Carr |

FOREIGN PATENT DOCUMENTS

| | | |
|---|---|---|
| CA | 1137514 | 2/1982 |
| DE | 1569440 | 6/1969 |
| EP | 003 303 | 8/1979 |
| EP | 031 423 | 7/1981 |
| EP | 652 201 | 5/1995 |
| EP | 934 922 | 8/1999 |
| EP | 1 063 221 | 12/2000 |
| GB | 1 192 121 | 5/1970 |

| GB | 1 450 632 | 9/1976 |
| GB | 1 517 585 | 7/1978 |
| GB | 1 567 638 | 5/1980 |
| JP | H02-048542 | 2/1990 |
| JP | 4154744 | 5/1992 |
| JP | H04-154744 | 5/1992 |
| JP | 2003-171328 | 6/2003 |
| JP | 2004026753 | 1/2004 |
| WO | WO 2007/053346 | 5/1992 |
| WO | 2007/065767 | 6/2007 |

OTHER PUBLICATIONS

U.S. Appl. No. 12/677,856's claims.*
Lowenkron, Steven, "Amines, Aromatic, Methylenedianiline", Kirk-Othmer Encyclopedia of Chemical Technology, 1992, p. 1-11.
H. J. Twitchett, "Chemistry of the Production of Organic Isocyanates" Chem. Soc. Rev. 3(2), 209-230, (1974).

* cited by examiner

*Primary Examiner* — Duc Truong
(74) *Attorney, Agent, or Firm* — Robert A. Diaz (57) ABSTRACT

Process for the production of di- and poly(diamino diphenyl methane) comprising the steps of
(a) reacting aniline and formaldehyde in the presence of an acid catalyst to produce a reaction mixture containing di- and polyamines;
(b) neutralizing the reaction mixture containing di- and polyamines;
(c) separating the neutralized reaction mixture into an organic phase containing di- and polyamines and an aqueous phase;
(d) further treating the organic phase separated off in step (c) by (d1) washing with water followed by (d2) separating the washed mixture into an organic phase and an aqueous phase and (d3) further fractionation of the organic phase to produce purified di- and polyamines on the one hand and aniline/water on the other hand;
(e) further treating the aqueous phase separated off in step (c) by (e1) washing with aniline followed by (e2) separating the washed mixture into an aqueous phase and an organic phase and (e3) further treatment of the aqueous phase to remove the aniline thereby leaving an effluent stream wherein phase separation in step (c) and/or step (e2) is facilitated by using any of the following methods either on its own or in combination with one or more of the other methods:
(A) removal of some of the water from the neutralized reaction mixture obtained in step (b) or the aqueous phase separated in step (c);
(B) addition of inorganic salt to the neutralized reaction mixture obtained in step (b) or the aqueous phase separated in step (c);
(C) return of some of the aqueous phase obtained in step (e2) or (e3) to the neutralized reaction mixture obtained in step (b) or to the washed mixture in step (e1).

14 Claims, 7 Drawing Sheets

PROCESS FOR PRODUCTION OF DI- AND POLYAMINES OF THE DIPHENYLMETHANE SERIES

CROSS REFERENCE TO RELATED APPLICATIONS

This application is the National Phase of International Application PCT/EP2008/061349 filed Aug. 28, 2008 which designated the U.S. and which claimed priority to European (EP) Pat. App. No. 07116764.7 filed Sep. 19, 2007. The noted applications are incorporated herein by reference.

Methylene diphenylene diisocyanate isomers (MDI) and the mixtures of the diisocyanates with higher molecular weight homologues known as poly-(methylene diphenylene diisocyanate) (hereinafter PMDI) are widely used as specialty binders for various composite materials, with polyamines for polyureas and, together with polyether and polyester polyols, to form the diverse range of polyurethane materials including cross-linked rigid foams for insulation, flexible foams for automotive seating and furniture and as elastomers & coatings. The isocyanate itself can be used as the binder for a range of other materials such as wood pieces in various forms and granulated rubbers in the manufacture of various composite products. PMDI is conventionally produced by phosgenation of the corresponding mixture of polyamines known as poly-(diamino diphenyl methane) (hereinafter DADPM) formed from condensation of aniline and formaldehyde.

Methods which have been described for the production of DADPM are numerous and varied. Condensation of aniline and formaldehyde (as the aqueous solution called formalin, as gaseous formaldehyde or as the solid paraformaldehyde) can take place in neutral, basic or acidic conditions, though conversion through to the required polymeric primary amine product mixture invariably requires the use of acidic species (even if, in the reaction conditions, they may be deemed to be present in their salt forms). The formalin may be used as received or may be further concentrated by fractionation, either by fractional distillation (for example EP 934922 and EP 1063221) or by means of a membrane-based process (for example U.S. Pat. No. 4,067,805 and EP 652201). The more dilute fraction produced in these processes may be used as such or may be disposed of.

Condensation of aniline with formaldehyde under neutral or basic conditions produces so-called neutral condensate, containing N,N'-methylene dianiline (aminal) and possibly other anilinoacetals. The neutral condensate is then subsequently converted to secondary amines and the final primary amine mixture by using acidic species. Many embodiments of such processes have been described including optional separation of water from the neutral condensate and optionally further drying of the condensate prior to acid addition (e.g. in U.S. 2006/287555 where processing a multiphase reaction system created upon addition of the acid can be avoided by achieving a reaction mixture of defined composition following water removal from the aminal). Heterogeneous solid acid catalysts have been described (e.g. in U.S. Pat. Nos. 3,362,979, 4,039,580 and 4,039,581), as have a range of homogeneous acids and, predominantly, aqueous mineral acids especially aqueous hydrochloric acid. Aniline hydrochloride solid (see, e.g., U.S. Pat. No. 4,297,294 and EP 3303) and gaseous hydrogen chloride (U.S. Pat. No. 3,676,497) have also been described.

Alternatively, condensation of aniline and formaldehyde directly under acidic conditions produces predominantly secondary amines which are subsequently converted to the desired primary amines by the already-in-place catalyst. A range of homogeneous acids and, predominantly, aqueous mineral acids such as sulphuric acid have been described but aqueous hydrochloric acid is predominantly employed for commercial scale production of DADPM. Extra acid may optionally be added during the process. Extensive prior art exists on ways and means of carrying out the reaction for example to manipulate the composition of the final polyamine mixture or to improve the process economics or to overcome processing problems.

Extensive prior art exists for separating the acidic reaction mixture into organic and aqueous phases by addition of extra amine or by use of sufficient water in the process or by removal of some water or by addition of various inorganic salts or by addition of water-immiscible [hydrophobic] organic solvents or combinations of these processing steps (e.g. EP 31423, GB 1450632, GB 1567638, U.S. Pat. Nos. 3,996,283, 4,094,907, 4,130,588, 5,196,591, 5,359,141, 5,679,841, 5,684,180, U.S. 2006/287555). Benefits of such process variations arise because at least a portion of the acidic catalyst may be returned to the start of the reaction, thus decreasing catalyst use. The composition of the separated organic phase may also thus be manipulated in beneficial ways. However, such process variations add significant extra complexity to the process. For the return of the acidic catalyst, additional processing equipment, which must be corrosion resistant, is required and the catalyst return is inevitably accompanied by some recycle of amine components which must be compensated for. In cases where additional water-immiscible chemicals such as chlorinated hydrocarbon solvents are employed, additional process streams are also generated, inevitably leading to further process complexity and cost. Thus, such methods are rarely used in practice for large-scale commercial production of polyaromatic polyamines such as DADPM.

Alternatively, the acidic catalyst may be partly neutralised during the process in order to achieve a claimed improvement in the colour of the polyisocyanates derived by phosgenation of the polyamines produced by the disclosed method (U.S. Pat. No. 6,031,136). At the end of the reaction, further base is added to complete the neutralisation, whereupon the organic and aqueous phases separate due to density differences and can be worked up.

Despite the extensive and varied methods described in the prior art and summarised above, large scale commercial production of DADPM is carried out predominantly according to the general principles described below. Thus, conventionally, at the end of the aniline/formaldehyde reaction, the acid catalyst is neutralised completely. Many possible neutralisation agents have been described but typically sodium hydroxide is used. The resulting mixture thus predominantly consists of unreacted aniline, the complex mixture which is the polyamine product, water and sodium chloride. The organic and aqueous (brine) phases separate because of the differences in their densities. Economic advantages which could arise from the use of lower levels of acid can not be realised because the salt water resulting from the subsequent neutralisation has a density too close to that of the organic mixture to permit ready phase separation. Thus, the ability to achieve a ready phase separation is an absolute requirement for operation of the conventional DADPM process in large, complex industrial plant.

The separated first organic phase is subsequently washed by addition with mixing of a hot aqueous stream, preferably water. Subsequent separation of the phases produces a weak brine stream and a second organic phase essentially free of sodium chloride from which unreacted aniline and water are subsequently removed by fractional distillation (see GB 1517585). This work-up procedure produces the required polyamine mixture in a condition suitable for subsequent use. The first separated brine phase will contain aniline and will, in practice, still contain some DADPM. Thus, addition with mixing of additional aniline to this brine phase is frequently carried out at industrial scale. Subsequent separation of the phases produces a brine stream containing aniline but essentially free of DADPM and a second organic phase consisting predominantly of aniline together with the DADPM removed from the first brine phase. Many examples of variations on the conventional process comprising acid catalysed reactions followed by neutralisation with base and ready separation of the phases on the basis of their relative densities are disclosed in the prior art [see for example U.S. 2006/094897, U.S. 2003/045745, U.S. Pat. No. 6,031,136 and references therein].

Addition of organic solvents such as hydrocarbons or halohydrocarbons (such as toluene, xylenes, monochlorobenzene, etc.) in the work-up stages of the process has been used to improve the separation of organic and aqueous phases (see, e.g., DE 1569440) or to improve the quality or composition of the separated organic phase by separation of a tarry layer (GB 1192121). Likewise, the separated aqueous brine phase can subsequently be extracted with organic solvents such as benzene or toluene [JP 04-154744, JP 2004-026753] but the presence of such additional chemicals results in the generation of additional process streams, requires separation and recovery of the solvent and inevitably leads to further process complexity and cost. Thus, such methods are rarely used in practice for large-scale commercial production of polyaromatic polyamines such as DADPM.

Conventionally, at the end of the aniline/formaldehyde reaction, the acid catalyst is neutralised completely without the addition of further substances [as mentioned in U.S. 2006/287555] i.e. the subsequent separation of phases occurs solely on the basis of density differences.

Similar processes also exist for condensing aromatic amines other than aniline with formaldehyde. Mixtures of aromatic amines including aniline may also be condensed with formaldehyde. These also require reaction with acidic species and, when this is using mineral acids (typically aqueous hydrochloric acid) and subsequent neutralisation with base (typically aqueous sodium hydroxide solution), then such circumstances clearly follow the techniques and limitations of the conventional DADPM process.

Figure 1:
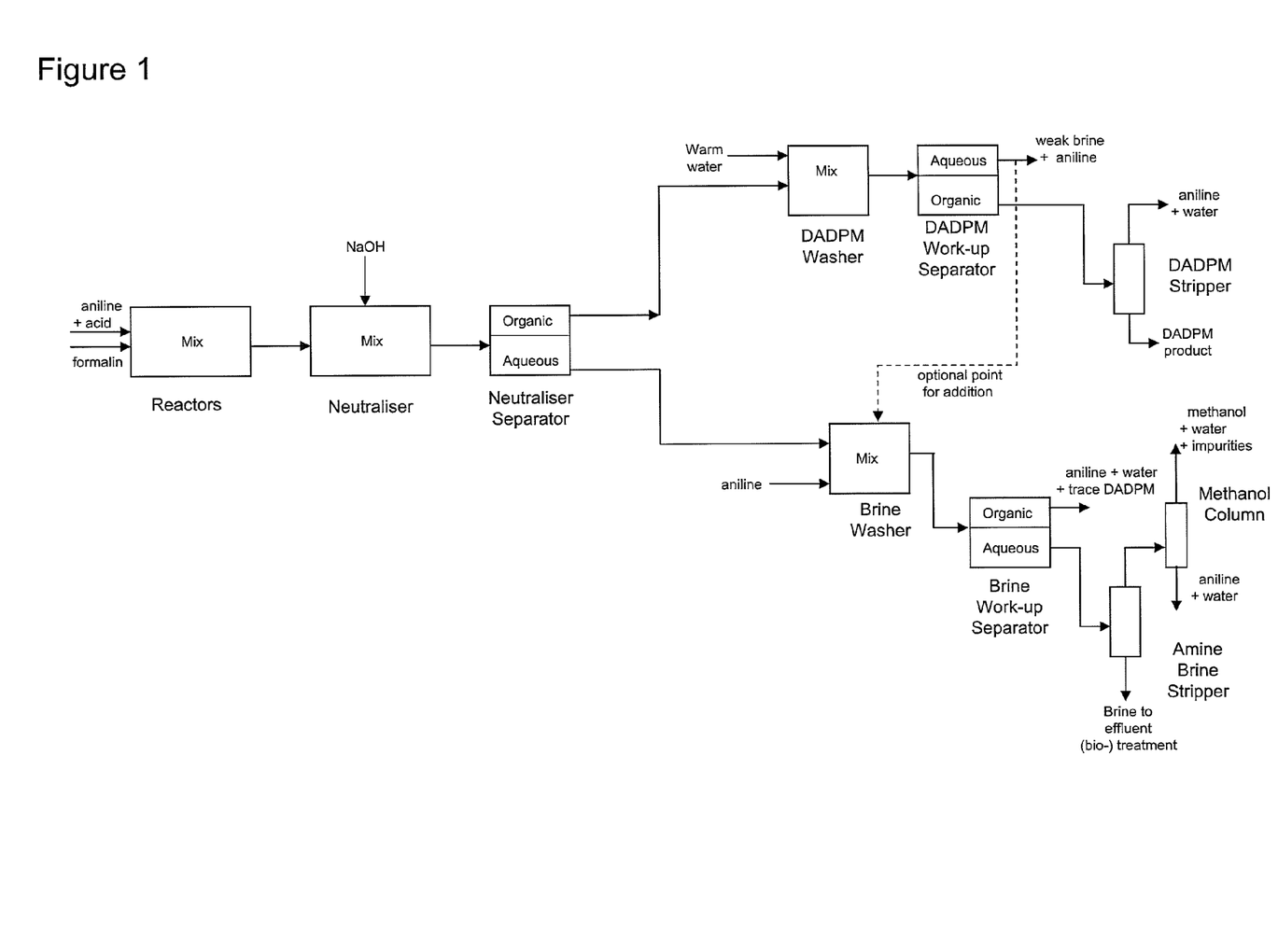
FIG. 1 is a schematic representation of a conventional process for making DADPM.

Thus, the following description of a conventional process based on the condensation of aniline with formaldehyde (as formalin) with aqueous hydrochloric acid as the catalyst and aqueous sodium hydroxide as the neutralising agent is provided for clarity but it is to be understood not to limit the scope of the invention. FIG. 1 is also provided to assist the description but is not limiting in any way. It is also to be understood that variations to the following description and descriptive terms may be encountered in practice but the principle stages and operations are recognisable to those skilled in the art.

Aniline is mixed with aqueous hydrochloric acid. Subsequently, formalin is added under controlled conditions of temperature and mixing to produce the required mixture of secondary amines containing various amino-benzyl-anilines, whilst limiting formation of well known impurities such as N-methylated species, N-formylamines, formic acid and formates and various types of so-called "quinazolines" to acceptably low levels. The complex reaction mixture is then heated to facilitate the rearrangement [so-called "isomerisation"] of the secondary amines to the required primary amines. The process conditions and equipment configurations to carry out this well known process are many and varied and include batch, semi-batch, semi-continuous and continuous processes, with variations on temperatures, pressures and temperature/pressure/time gradients. All these process variations, together with variations of the aniline-formaldehyde-HCl recipe and variations in the methods of their combination (e.g. staged or split additions of reagents) lead to many possible mixtures of primary amine homologues and isomers, all well known to those skilled in the art, and are simplified to "Reactors" in FIG. 1.

When the concentration of amino-benzyl-aniline-type species is sufficiently low, as determined by on-line or off-line analysis or operational experience, the reaction is deemed to be complete and the acidic mixture is neutralised.

According to the prior art, the neutralization is conventionally conducted at temperatures of, e.g., from 90 to 100° C. (H. J. Twitchett, Chem. Soc. Rev. 3(2), 223 (1974). The hydroxides of the alkali and alkaline earth elements are examples of suitable bases. Aqueous NaOH is preferably used and, optionally, with the inorganic base in excess to ensure no acidic streams pass to parts of the production plant not designed to withstand the corrosive effects of such a material. Staged, partial neutralisation is also known (U.S. Pat. No. 6,673,970).

After neutralisation, the organic phase (predominantly aniline and DADPM) and aqueous phase (predominantly aqueous sodium chloride solution—the so-called brine) separate due to density differences in the Neutraliser Separator, the brine phase on the bottom due to its higher density. In large scale production, the separate phases typically undergo individual washing stages as this is usually preferable to attempting sufficient separation in a single stage and ensures both the organic stream and aqueous brine stream going forward in the process contain minimal quantities of the other phase.

Thus, the organic layer is washed in the DADPM Washer by addition of a certain quantity and quality of water to remove residual salt species, such as sodium chloride and sodium hydroxide. A temperature in excess of approximately 70° C. is required to overcome the problem of formation of the well-known $[4,4'-MDA]_3.NaCl$ complex (GB 1517585). The organic and aqueous layers separate in the DADPM Work-up Separator due to density differences, the organic phase on the bottom due to its higher density. The low density weak brine stream produced will, of course, contain some level of organic compounds depending on their solubilities and so is treated within the process, typically by addition to some other suitable stream. The organic stream is then separated by fractionation, typically by distillation in a DADPM Stripper column, to produce the purified DADPM product ready for use as such or for conversion to the corresponding polyisocyanate mixture by phosgenation or other means. The separated stream of predominantly aniline and water can be further treated and the aniline recycled to the start of the process. The consequences of feeding aniline and water forward to the phosgenation plant are obvious and well-known (see, for example, Ulrich in "Chemistry and Technology of Isocyanates", John Wiley & Sons, New York, 1996).

Likewise, the crude brine phase from the Neutraliser Separator is washed in the Brine Washer by addition of an organic solvent in order to remove residual organic species. Any suitable solvent, for example toluene, monochlorobenzene or other suitable hydrocarbon, can be used. However, use of aniline as the washing solvent obviates the need for use of an extra chemical in the production process. A temperature in excess of approximately 70° C. is required to overcome the problem of formation of the well-known $[4,4'-MDA]_3.NaCl$ complex. Optionally, the aqueous stream from the DADPM Work-up Separator, containing predominantly water, aniline and a relatively small amount of sodium chloride, may be added here. The organic and aqueous layers separate in the Brine Work-up Separator due to density differences, the brine phase on the bottom due to its higher density. The washed brine will contain the washing solvent at its own solubility level and, thus, must be further treated, typically by fractional distillation to remove the solvent and, when this is aniline, in a fractional distillation unit known as the Amine Brine Stripper. The fractional distillation may optionally be performed with associated steam injection (steam stripping). Some water is also simultaneously removed from the brine. The distilled solvent stream can be further treated elsewhere in the process and, if the solvent is aniline, it can be recycled to the start of the process. The brine can be further treated, for example by bio-treatment, to reduce levels of organic contaminants to very low levels for subsequent discharge, for example, to the sea. The aniline used for the washing leaves the Brine Work-up Separator containing minor amounts of DADPM and saturated with water, thus making it particularly suitable as the absorbent or part of the absorbent for gaseous HCl if this is to be used in the process as exemplified in WO 2007/065767.

Methanol, typically present in the original formalin, generally follows the aqueous phase in the various separations. One way of dealing with this impurity is at the Amine Brine Stripper, where it is vaporised and thus forms part of the predominantly aniline-water stream. Other volatile organic impurities for example cyclohexanol, cyclohexylamine, dicyclohexylamine also concentrate in this stream. Fractionation of this stream, optionally by fractional distillation for example in a so-called "Methanol Column", produces an aniline-water stream which can be recycled to the process and a waste stream of methanol and other impurities which may be disposed of, optionally by incineration. This stream may also contain a significant amount of water which is thus an alternative route for water out of the DADPM process compared to the final brine stream.

A further option is to further fractionate the methanol-water stream, optionally by a membrane-based process such as pervaporation, into a water-rich stream and a methanol-rich stream which contains most of the other organic impurities. The water-rich stream is thus significantly reduced in organic content and may be passed directly to the final effluent or treated further whilst the methanol-rich stream is significantly reduced in water and thus can be incinerated more cheaply.

Thus the two main streams leaving the plant are the DADPM product stream and the clean brine stream. The various streams containing aniline and water plus other components such as DADPM, sodium chloride, sodium hydroxide and various impurities can be treated individually or combined in various ways known to those skilled in the art to enable aniline to be recycled to the start of the process by cost effective means. The recycle aniline may optionally contain water and DADPM and impurities at levels low enough not to impact detrimentally on the main production process. A purge stream of impurities (such as, for example, methanol, cyclohexanol, cyclohexylamine, etc) may also be generated.

Process and equipment configurations for all these so-called work-up processes are many and varied and are well known to those skilled in the art. For example, each of the mixing and associated separation operations can be in separate vessels or can be within a single unit. The densities of the various streams may be monitored by on-line density meters of various designs or may be calculated based on the anticipated composition and the measured temperature of the stream.

It can be seen from the above description that crucial to the work-up stages of commercial production of DADPM are the various organic/aqueous phase separations and that these are conventionally based on density differences.

The densities of the organic and brine phases depend on the ratios of aniline, formaldehyde, HCl and NaOH used, the amount of water present (dependent upon the concentrations of all the aqueous reactants and the water produced by the condensation of aniline and formaldehyde) and the operating temperatures. In the washing stages, additional factors influencing the densities of the organic and aqueous phases are the relative amounts of the washing streams. It is to be understood that the presence of impurities in any of the reactants, reaction mixtures or other process streams, for example methanol, cyclohexanol, cyclohexane, can influence the density separations but such variations are not described explicitly here. Operational problems can be encountered in the various phase separation stages of the process when the densities of the organic and aqueous phases become similar, such that the phases will not separate or will not separate in a timescale which is commercially viable.

In particular, decreasing the amount of acid catalyst with subsequent decrease of NaOH for neutralisation whilst providing extra thermally-controllable residence time to maintain the same or substantially the same polyamine product mixture composition can be economically beneficial, but the resulting brine will have lower density than from a higher acid process. Thus, there will be a limitation on the decrease in catalyst level which can be achieved when problems arise in the organic/aqueous separations.

It is to be understood that these separation difficulties can occur in any of the separators, either individually or simultaneously in more than one separator and will be specific to the exact combination of factors (aniline/formaldehyde/acid ratios, formalin strength, acid strength, stream temperatures, volume and composition of various streams within the process and, thus, overall design of the total process, etc.) and, thus, that the object of the present invention is to provide means to overcome the problems of insufficient density difference to separate aqueous and organic phases in the industrial scale production of DADPM. Manipulation of the density difference between aqueous and organic phases can not be overcome with significant changes in the temperatures of the phases without attracting significant extra costs in terms of energy use and other problems such as the increasing mutual solubility of the phases in each other at higher temperatures and the problem of formation of $[4,4'\text{-}MDA]_3.NaCl$ solids at lower temperatures.

U.S. 2007/0179317 teaches that separation of the neutralised reaction mixture can be supported by the addition of aniline and/or water. However, there are certain serious limitations inherent in such an approach:—

When decreasing the amount of acid catalyst used in the process, thus decreasing the amount of neutralising NaOH and, hence, decreasing the density of the brine phase, addition of extra aniline will indeed decrease the density of the organic phase and, thus, can maintain the density difference required for separation of the phases. However, the extra aniline will increase the amount of aniline which must be removed from the DADPM product, thus increasing the capital and operating costs of the production plant.

When decreasing the amount of acid catalyst used in the process and, thus, decreasing the amount of neutralising NaOH and, thus, decreasing the density of the brine phase, addition of sufficient extra water will decrease the density of the brine still further, eventually reaching the point where the density differences are such that the brine has lower density than the organic phase (so-called "phase inversion" or "flipping" of the phases). Thus, the phases can be separated but the brine phase is now so dilute that the subsequent separation from aniline in the still-required washing stage (to remove DADPM) is problematic and, in addition, there is a still greater total volume of effluent to be dealt with.

Thus, it is an object of the present invention to provide an economically beneficial process to overcome the problems of insufficient density difference to separate aqueous and organic phases in the industrial scale production of DADPM, especially when operating low acid DADPM processes. Here, low acid indicates a molar ratio of HCl to formaldehyde [expressed as $CH_2O$ equivalents] from about 0.1 to about 0.2 and applies for DADPM manufacture using aniline to formaldehyde molar ratios in the range from about 2.0 to about 3.5.

It has now surprisingly been found that the object of the present invention can be provided by means of modifying the density of the aqueous phase without recourse to utilisation or formation of any additional chemicals or chemical mixtures beyond those that are present as products of the conventional DADPM process nor by any means which imparts the further problems to the overall production process as is the case with the above described prior art.

According to the present invention the density of the aqueous phase is modified by using any of the following methods, either on its own or in combination with one or more of the other methods:

(a) The density of the aqueous phase can be increased by removal of some of the water from the neutralised reaction mixture as further exemplified in Methods 1 and 2 below;

(b) The density of the aqueous phase can be increased by addition of a suitable quantity of solid sodium chloride or a concentrated aqueous solution of sodium chloride as further exemplified in Method 3 below;

(c) The density of the aqueous phase can be increased by return of a brine stream of greater density generated from a weaker brine stream from within the process itself as further exemplified in Method 4, 5 and 6 below.

BRIEF DESCRIPTION OF THE FIGURES

FIG. 8 is a schematic representation of a DADPM process with density manipulation of the brine phase using a combination of evaporation and brine recycle including a membrane-based method of brine concentration.

The various embodiments of the present invention are described below and with reference to the schematic figures provided. Methods of modifying the density of the organic phase are also possible (as described in the patentee's co-pending patent application of even date) and can be used in combination with the presently claimed methods of modifying the density of the aqueous phase. It is to be understood that the Figures constitute part of the present invention but are not intended to be limiting in any way in terms of, for example, process engineering and process design. The different embodiments and further methods are referred to as numbered Methods (Method 1, Method 2, etc.) but it is to be understood that this is solely for the purposes of convenience and that the present invention encompasses all of the described embodiments for modifying the density of the aqueous phase and their combinations and variations with each other and with other embodiments or methods.

Method 1: The aqueous phase density can be increased by removal of some of the water together with some aniline from the neutralised reaction mixture by fractionation, preferably by evaporation from the Neutraliser (FIG. 2) thus ensuring proper operation of the Neutraliser Separator. The heat from the energy of neutralisation may provide all or some of the energy requirement for this process. Additional heat may be added by any suitable means. The exact conditions for the operation of the Neutraliser can be determined by those skilled in the art but can be at approximately 100° C. and atmospheric pressure or may be at higher temperatures and pressures.

Figure 3:
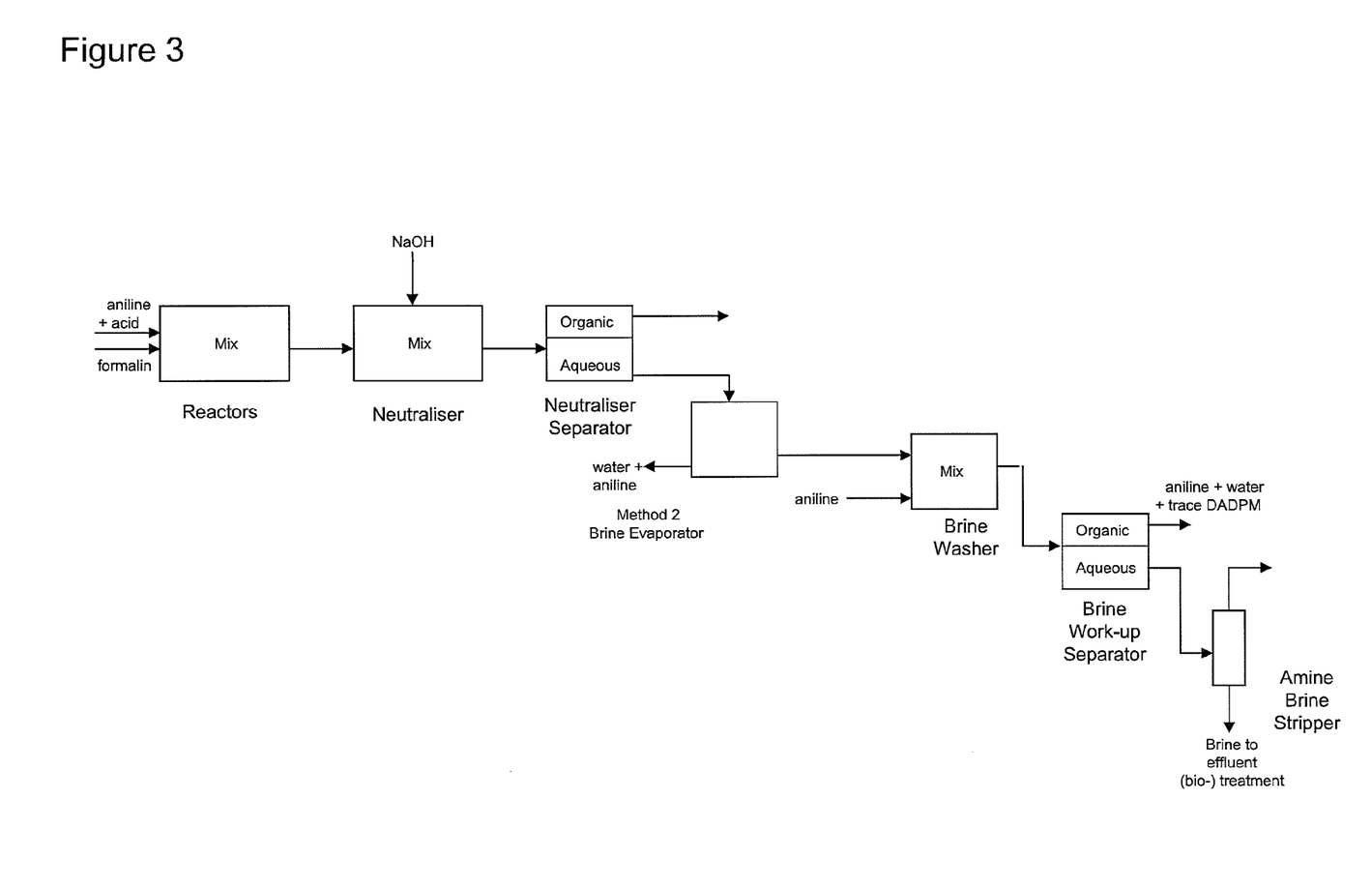
FIG. 3 is a schematic representation of a DADPM process with density manipulation of the brine phase using Method 2

Method 2: Removal by fractionation, optionally by fractional distillation (for example by evaporation in a so-called Brine Evaporator), of some of the water from the crude brine, thus increasing its density, after separation from the crude neutralised organic reaction mixture in the Neutraliser Separator prior to washing thus ensuring proper operation of the Brine Work-up separator (FIG. 3).

Method 3: The density of the brine in the process may be increased by addition of a suitable quantity of solid sodium chloride or a concentrated aqueous solution of sodium chloride, optionally at a controlled temperature and with mixing, at a suitable point in the process for example prior to the Neutraliser Separator for example by addition to the Neutraliser (FIG. 4) thus ensuring proper operation of the Neutraliser Separator. Optionally, the addition may be made to another suitable point such as the Brine Washer to ensure proper operation of the Brine Work-up separator.

Method 4: Return of some of the brine to the process, thus increasing the density of subsequent aqueous phase streams containing predominantly sodium chloride and water, preferably prior to the separation of the crude neutralised organic reaction mixture and the crude brine for example by addition to the Neutraliser (FIG. 4) thus ensuring proper operation of the Neutraliser Separator. Optionally, the addition may be made to another suitable point such as the Brine Washer to ensure proper operation of the Brine Work-up separator. The brine being returned is more dense than the brine forming from neutralisation of the reaction mixture because of the water removal via the Amine Brine Stripper—Methanol Column route, which may optionally be further enhanced with additional equipment in order to increase the amount of water being removed.

Figure 5:
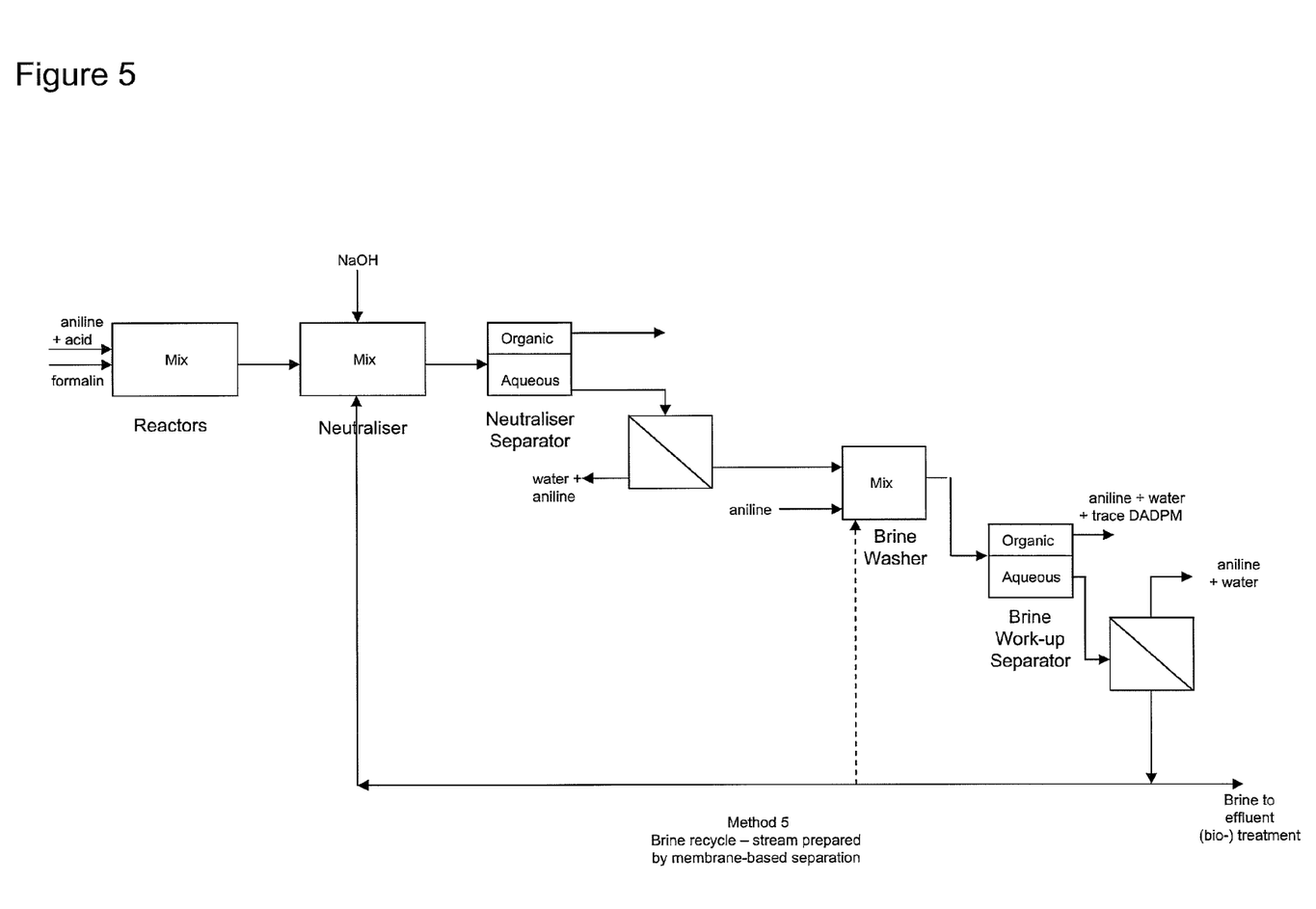
FIG. 5 is a schematic representation of a DADPM process with density manipulation of the brine phase using Method 5.
Figure 6:
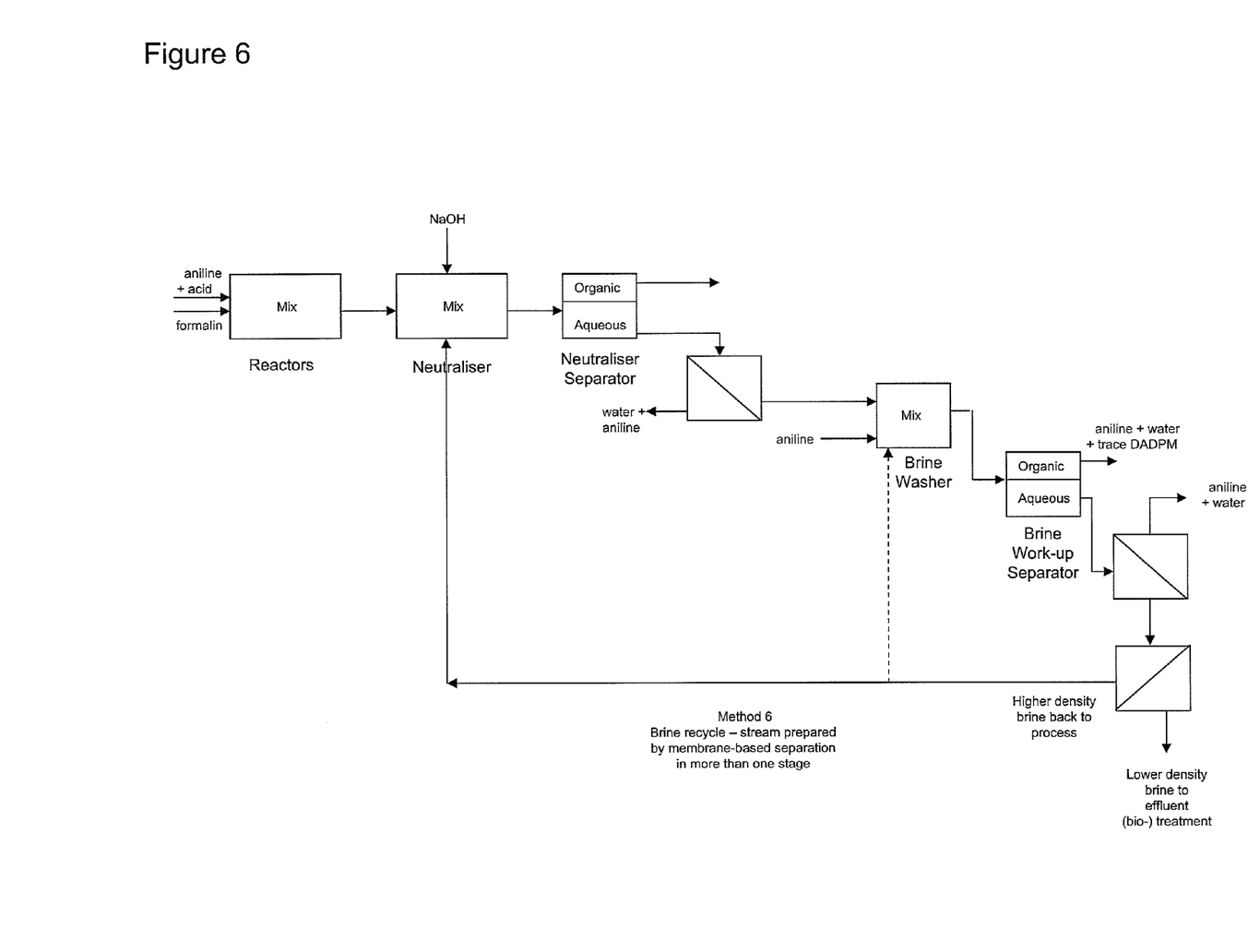
FIG. 6 is a schematic representation of a DADPM process with density manipulation of the brine phase using Method 6.

Method 5: Return of some of the brine to the process, thus increasing the density of subsequent aqueous phase streams containing predominantly sodium chloride and water, preferably prior to the separation of the crude neutralised organic reaction mixture and the crude brine for example by addition to the Neutraliser thus ensuring proper operation of the Neutraliser Separator where the concentration of sodium chloride has been increased by fractionation of a more dilute brine stream, optionally by a membrane-based fractionation process, optionally by reverse osmosis or electrodialysis or the like (FIG. 5). Optionally, the addition may be made to another suitable point such as the Brine Washer to ensure proper operation of the Brine Work-up separator. The concentrated brine may optionally be concentrated still further by one or more additional concentration stages, optionally using membrane-based processes (Method 6) (FIG. 6).

Additional embodiments of the present invention can be defined by means of combinations of these methods and their variations. Non-limiting examples include:—

Figure 7:
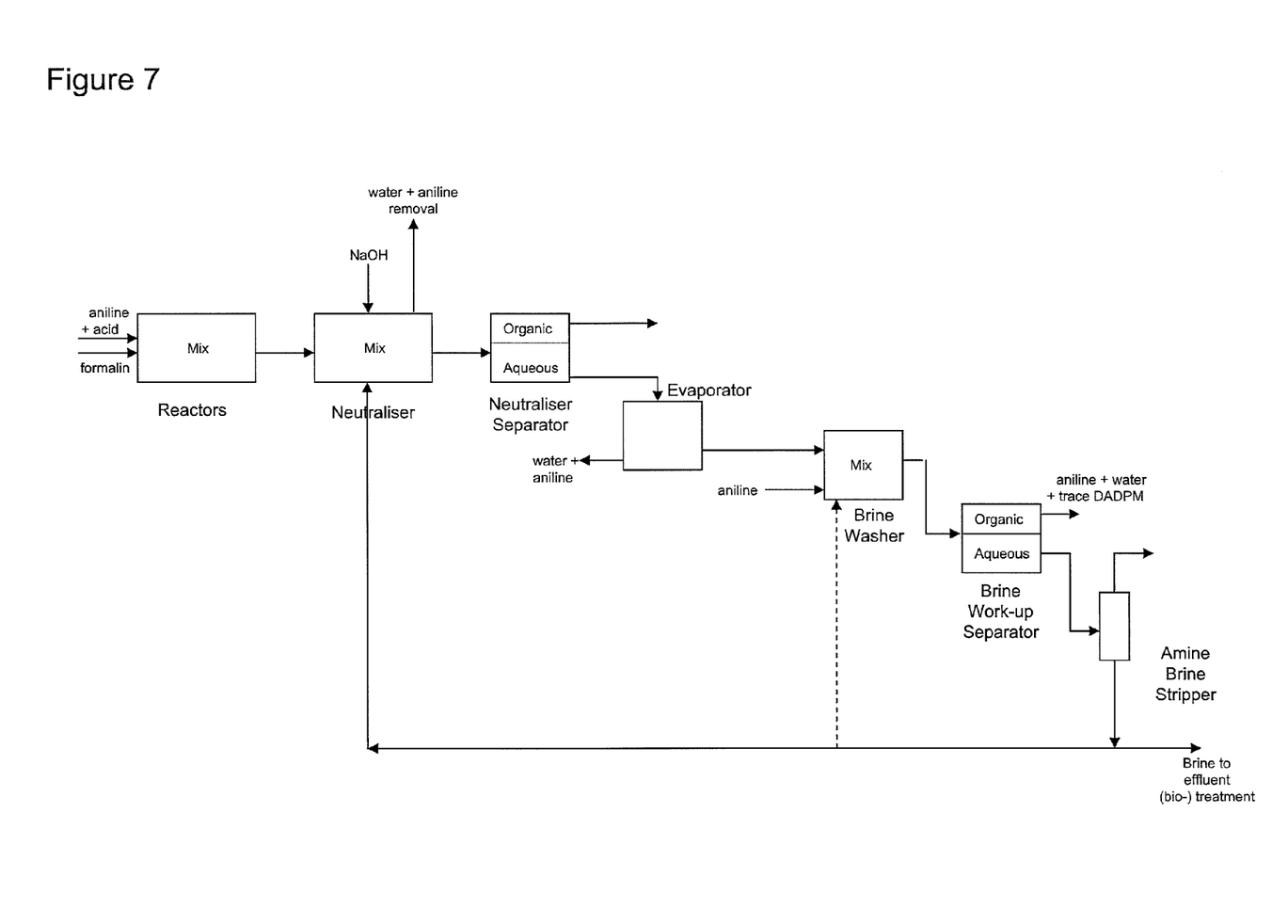
FIG. 7 is a schematic representation of a DADPM process with density manipulation of the brine phase using a combination of evaporation and brine recycle.

Combination example 1 [Method 7]: Return of some of the brine to the process, thus increasing the density of subsequent aqueous phase streams containing predominantly sodium chloride and water, preferably prior to the separation of the crude neutralised organic reaction mixture and the crude brine for example by addition to the Neutraliser where the concentration of sodium chloride has been increased by fractionation of a more dilute brine stream, optionally by fractional distillation (for example by evaporation) (FIG. 7).

Combination example 2 [Method 8]: Return of some of the brine to the process, thus increasing the density of subsequent aqueous phase streams containing predominantly sodium chloride and water, preferably prior to the separation of the crude neutralised organic reaction mixture and the crude brine for example by addition to the Neutraliser thus ensuring proper operation of the Neutraliser Separator where the brine is first treated by fractionation, optionally by fractional distillation such as evaporation or a membrane-based process to remove all or essentially all of the aniline, optionally together with removal of some of the water, and the brine is then further treated by fractionation, optionally by fractional distillation or a membrane-based process optionally by reverse osmosis or electrodialysis or the like to generate a more concentrated brine stream (FIG. 8)

It is to be understood that other variations of the embodiments and combinations of two or more of these embodiments or their variations for modifying the density of the aqueous phase, whether explicitly described or not, are to be considered within the scope of the present invention. Examples of such variations include but are not limited to return of various streams to parts of the process other than those mentioned specifically, for example, to lines connecting vessels rather than vessels themselves and use of additional mixing devices such as dynamic or static mixers where deemed to be advantageous by those skilled in the art. Variations to the process embodiments of the present invention and their operation can also be understood to exist at the start-up or shut-down of the DADPM plant or when the plant is held in a so-called "idle mode" during short-term production interruptions.

Further differences to the specifics of the description given above but which constitute further embodiments of the present invention occur when the process of producing DADPM includes the use of gaseous hydrogen chloride from whatever source rather than or in combination with the use of aqueous hydrochloric acid and when different concentrations and qualities of aniline and formalin are used.

More detailed descriptions of the main embodiments of the present invention and the other methods are described below and with reference to the schematic figures provided.

Figure 2:
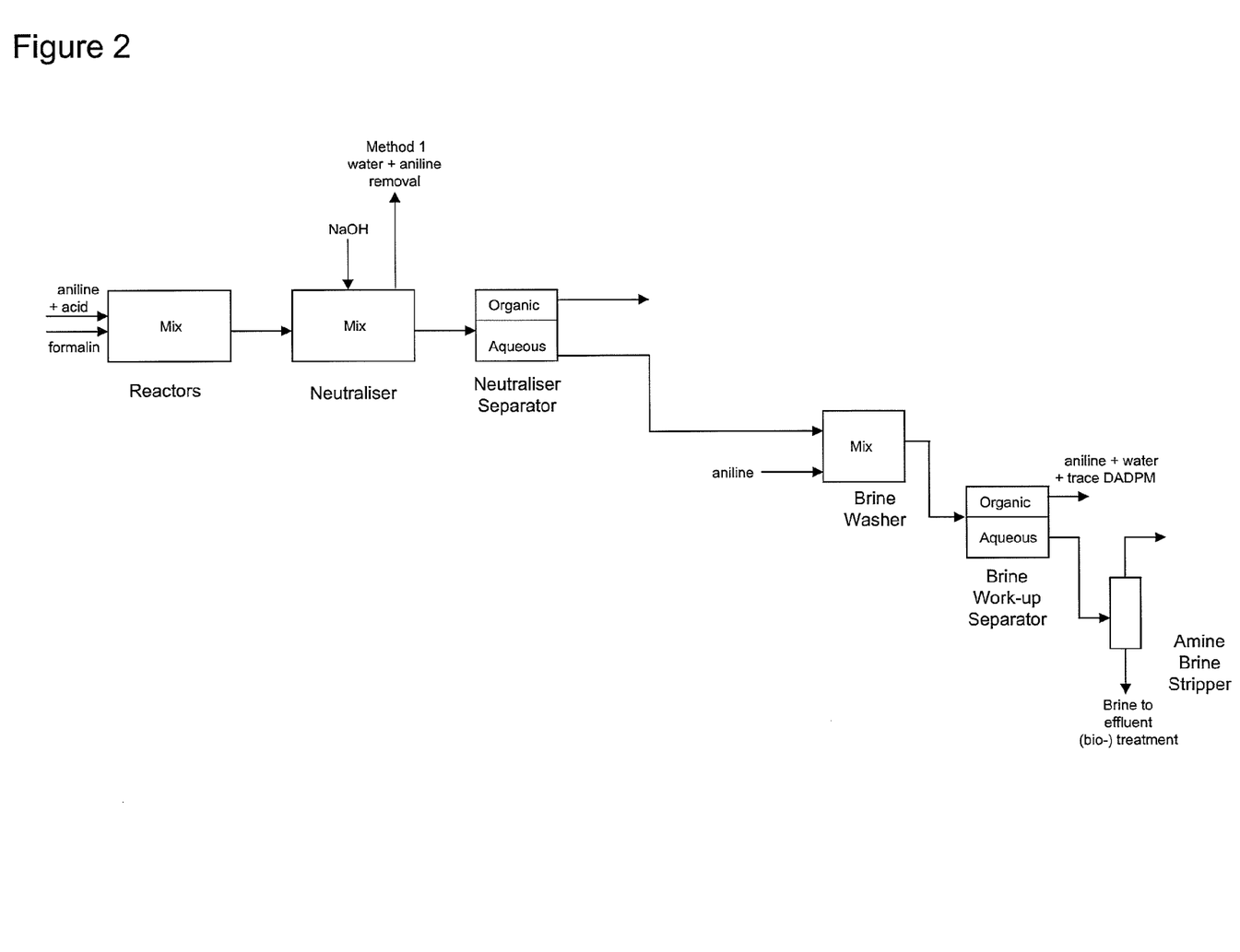
FIG. 2 is a schematic representation of a DADPM process with density manipulation of the brine phase using Method 1.

Method 1: Decreasing the amount of acid catalyst with subsequent decrease of NaOH for neutralisation can be economically beneficial, but the resulting brine will have lower density than from a higher acid process. Thus, there will be a limitation on the decrease in catalyst level which can be achieved when problems arise in the organic/aqueous separations. This limitation can be overcome, thus facilitating increased economic benefits, by removing some of the water, preferentially as vapor, from the Neutraliser (FIG. 2). This may be carried out by means of simply venting the vapor from the Neutraliser via a line to another suitable part of the process or extra heat may be added to the neutralised mixture by means of circulation of the mixture or part of the mixture through a reboiler. Some aniline is also normally removed with the water, thus providing a means of increasing the density of the organic phase if required, for example, when operating high aniline/formaldehyde recipes. The water/aniline stream may be combined with other similar streams elsewhere in the plant.

Method 2: Decreasing the amount of acid catalyst with subsequent decrease of NaOH for neutralisation can be economically beneficial, but the resulting brine will have lower density than from a higher acid process. Thus, there will be a limitation on the decrease in catalyst level which can be achieved before problems arise in the organic/aqueous separations. This limitation can be overcome, thus facilitating increased economic benefits, by removing some of the water, preferentially as vapor by fractionation of the crude brine stream exiting the Neutraliser Separator, optionally by fractional distillation, preferably by evaporation (FIG. 3). Some aniline is also normally removed with the water. The water/aniline stream may be combined with other similar streams elsewhere in the plant.

Figure 4:
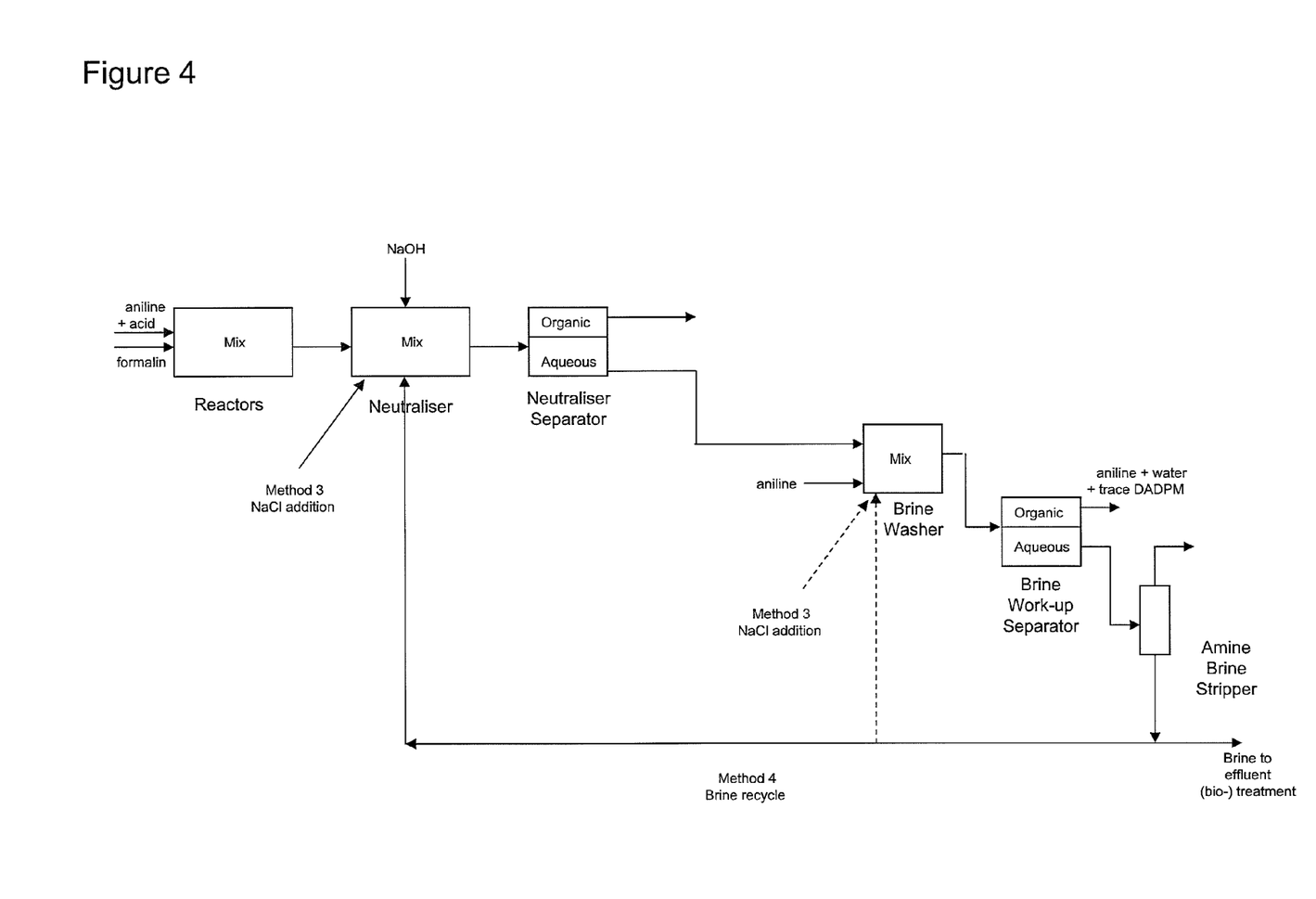
FIG. 4 is a schematic representation of a DADPM process with density manipulation of the brine phase by using either Methods 3 or 4.

Method 3: Decreasing the amount of acid catalyst with subsequent decrease of NaOH for neutralisation can be economically beneficial, but the resulting brine will have lower density than from a higher acid process. Thus, there will be a limitation on the decrease in catalyst level which can be achieved before problems arise in the organic/aqueous separations. This limitation can be overcome, thus facilitating increased economic benefits, by increasing the density of the brine phase for example in the Neutraliser Separator or in the Brine Work-up Separator by addition of solid sodium chloride or a concentrated aqueous solution of sodium chloride at a suitable point in the process for example by addition to the Neutraliser (FIG. 4).

Method 4: Decreasing the amount of acid catalyst with subsequent decrease of NaOH for neutralisation can be economically beneficial, but the resulting brine will have lower density than from a higher acid process. Thus, there will be a limitation on the decrease in catalyst level which can be achieved before problems arise in the organic/aqueous separations. This limitation can be overcome, thus facilitating increased economic benefits, by return of some of the brine to the process, thus increasing the density of subsequent aqueous phase streams containing predominantly sodium chloride and water, preferably prior to the separation of the crude neutralised organic reaction mixture and the crude brine for example by addition to the Neutraliser (FIG. 4). The brine to be returned is more dense than the brine forming from neutralisation of the reaction mixture because of the water removal via the Amine Brine Stripper—Methanol Column route.

Method 5: Decreasing the amount of acid catalyst with subsequent decrease of NaOH for neutralisation can be economically beneficial, but the resulting brine will have lower density than from a higher acid process. Thus, there will be a limitation on the decrease in catalyst level which can be achieved before problems arise in the organic/aqueous separations. This limitation can be overcome, thus facilitating increased economic benefits, by increasing the density of the brine phase for example in the Neutraliser Separator or in the Brine Work-up Separator by recycling a brine stream which has been produced by fractionation of the aqueous solution by means of membrane-based fractionation using semi-permeable membranes (FIG. 5). The fractionation may take place in one or more locations of the work-up system and may be membrane-based liquid-liquid separation or pervaporation or reverse osmosis or electrodialysis or other advanced membrane-based technique e.g. Memstill® or the like. The concentrated brine stream is preferably the retentate stream. The low density brine stream may be sent for disposal for example by bio-treatment before final disposal or may be still further treated, optionally by a membrane-based process such as reverse osmosis or electrodialysis or other advanced membrane-based techniques e.g. Memstill® to produce a clean or essentially clean water stream suitable for disposal to the natural environment and a more concentrated stream for incineration or sequestration in a deep well disposal facility or the like.

Method 6: The concentrated brine stream being recycled as described above may be generated from a more dilute brine stream by more than one stage (FIG. 6).

Methods 7 & 8: The density of the brine phase for example in the Neutraliser Separator or in the Brine Work-up Separator can be adjusted by addition of a more concentrated brine by a combination of other methods (FIGS. 7 & 8).

Many further combinations and variations of the various specifically described embodiments and other variations described above can be derived from the present invention by those skilled in the art.

The described process steps for making DADPM can be followed by the following steps in order to prepare PMDI:
(I) dissolving the worked-up DADPM in solvent, typically chlorobenzene, and reacting with phosgene, also optionally in the presence of solvent, to produce PMDI;
(II) working up and separating by known methods the PMDI product into the range of di-isocyanate isomers and PMDI mixtures.

The phosgenation reaction can be carried out by any of the many and well known variations described in the prior art.

For example, the DADPM can be dissolved in chlorobenzene to a level of typically 10 to 60 wt %, preferably 20 to 40 wt %, the resulting solution then being introduced into reaction vessels typically by means of special mixing devices by means of which the amine blend is thoroughly and intimately mixed with phosgene, also optionally in solution, preferably in the same solvent as the DADPM.

Reaction temperature at this stage is typically in the range 50 to 150° C., preferably 75 to 95° C. The product of this initial reaction stage may be worked up immediately or there may be additional reaction, optionally in additional reaction vessels, optionally including addition of phosgene, for further digestion of reaction intermediates and/or by-products. Many pressure and temperature regime variations are known from the prior art and many variations in process equipment can be employed.

On completion of the phosgenation reaction, the crude MDI product can be separated from excess phosgene, product HCl, and reaction solvent by any means known to those skilled in the art, typically by distillation, and subjected to further work up such as the well established thermal cracking of impurity compounds known as "dechlorination". The mixture of di-isocyanate isomers and PMDI homologues can be used as such or further refined to give various di-isocyanate or polymeric MDI products, typically by fractional distillation or fractional crystallisation. All these process steps can be carried out in batch, continuous or semi-continuous modes.

EXAMPLES

Reference Example

Conventional Process

In a stirred batch reactor, 132 g of 30.7% aqueous hydrochloric acid was added to 609 g of 99.9% purity aniline and the temperature was controlled to 50° C. 204 g of 47% formalin was then added over the course of 30 minutes controlling the temperature within the range 50-65° C. [An/F/HCl recipe of 2.05/1/0.35 molar]. The mixture was isomerised for 170 minutes during which time the temperature was increased to 137° C. This was followed by neutralisation with 92 g of 50.4% NaOH (=5% excess) at a temperature of 95° C., the mixture separated in an organic and aqueous phase (organic phase being the top layer).

The separated organic phase (695 g) was washed with 104 g water at 95° C. after which the mixture readily separated into organic and aqueous phases (the organic phase being the bottom layer). The organic phase (716 g) was worked up further by distillation to remove the aniline.

The separated aqueous phase (83 g) was added to the aqueous phase (344 g) from the neutraliser separator and washed with aniline (142 g). The mixture readily separated into organic and aqueous phases (the organic phase being the top layer). The separated organic and brine phases could then be further treated following the principles described in the text.

Comparative Example 1

Low Acid Process

In a stirred batch reactor, 67 g of 30.7% aqueous hydrochloric acid was added to 609 g of 99.9% purity aniline and the temperature was controlled to 50° C. 204 g of 47% formalin was then added over the course of 30 minutes controlling the temperature within the range 50-65° C. [An/F/HCl recipe of 2.05/1/0.18 molar]. The mixture was isomerised for 170 minutes during which time the temperature was increased to 170° C. This was followed by neutralisation with 47 g of 50.4% NaOH (=5% excess) at a temperature of 95° C., creating a mixture in which the phases did not readily separate.

Example 1

Low Acid Process Plus One Embodiment of the Present Invention

The neutralised non-separating mixture from Comparative Example 1 was treated by addition of 136 g of 20% NaCl solution which resulted in separation of organic and aqueous phases (the organic phase being the top layer). Here the brine was prepared directly by dissolving solid NaCl in water but other embodiments of the present invention include preparation of such a brine by recycling and concentrating previously separated brine.

The separated organic and brine phases could then be further treated following the principles described in the text.

Analysis of the organic material showed that the polymeric DADPM produced contained 54.5 wt % diamines, 24.5 wt % triamines, 11.4 wt % tetramines and 9.6 wt % higher oligomers.

The invention claimed is:

1. A process comprising the steps of:
   (a) reacting aromatic amine and formaldehyde in the presence of an acid catalyst to produce a reaction mixture containing di- and polyamines;
   (b) neutralising the reaction mixture containing di- and polyamines;
   (c) separating the neutralised reaction mixture into an organic phase containing di- and polyamines and an aqueous phase;
   (d) further treating the organic phase separated off in step (c) to produce purified di- and polyamines, optionally by (d1) washing the organic phase separated off in step (c) with water or other solvent followed by (d2) separating the washed mixture into an organic phase and an aqueous phase and (d3) further fractionation of the organic phase to produce purified di- and polyamines and aromatic amine/water;
   wherein the density of the aqueous phase in step (c) is increased by:
   (A) removing some of the water from the neutralised reaction mixture obtained in step (b) before the separation step (c); or
   (B) adding an inorganic salt to the neutralised reaction mixture obtained in step (b) before the separation step (c).

2. The process according to claim 1 wherein the aqueous phase separated off in step (c) is further treated by (e1) washing with aromatic amine or other solvent followed by (e2) separating the washed mixture into an aqueous phase and an organic phase and (e3) further treatment of the aqueous phase to remove the aromatic amine thereby leaving an effluent stream.

3. The process according to claim 2 wherein the phase separation in step (c) is further facilitated by a method (C): return of some of the aqueous phase obtained in step (e2) or (e3) to the neutralised reaction mixture obtained in step (b) or to the washed mixture in step (e1).

4. The process according to claim 1 wherein the process comprises the methods (A) and (B).

5. The process according to claim 1 wherein step (b) involves adding an excess of base to neutralise the remaining acid catalyst.

6. The process according to claim 1 wherein the acid catalyst is hydrogen chloride.

7. The process according to claim 1 wherein the acid catalyst is neutralised in step (b) by adding sodium hydroxide.

8. The process according to claim 1 wherein the aromatic amine is aniline and the aromatic polyamine is di- and poly (diamino diphenyl methane).

9. The process according to claim 8 wherein the acid catalyst is hydrogen chloride and the molar ratio of hydrogen chloride to formaldehyde [expressed as CH2O equivalents] is from about 0.1 to about 0.2 and the aniline to formaldehyde molar ratio is in the range from about 2.0 to about 3.5.

10. The process according to claim 1 wherein method (A) involves fractionation by evaporation or membrane-based fractionation, in step (b) and/or step (c).

11. The process according to claim 6 wherein the inorganic salt of method (B) is sodium chloride.

12. The process according to claim 1 wherein the aromatic polyamines in a subsequent step are phosgenated to obtain the corresponding aromatic polyisocyanates.

13. The process according to claim 7 wherein the inorganic salt of method (B) is sodium chloride.

14. A process comprising the steps of:
   (a) reacting aromatic amine and formaldehyde in the presence of an acid catalyst to produce a reaction mixture containing di- and polyamines;
   (b) neutralising the reaction mixture containing di- and polyamines;
   (c) separating the neutralised reaction mixture into an organic phase containing di- and polyamines and an aqueous phase;
   (d) further treating the organic phase separated off in step (c) to produce purified di- and polyamines, optionally by (d1) washing the organic phase separated off in step (c) with water or other solvent followed by (d2) separating the washed mixture into an organic phase and an aqueous phase and (d3) further fractionation of the organic phase to produce purified di- and polyamines and aromatic amine/water;
   (e) treating the aqueous phase separated off in step (c) by:
       (i) removing some of the water from the aqueous phase separated in step (c) before washing said aqueous phase in a subsequent washing step; or
       (ii) adding an inorganic salt to the aqueous phase separated in step (c) before washing said aqueous phase in a subsequent washing step;
   wherein the density of the aqueous phase in step (c) is increased by:
   (A) removing some of the water from the neutralised reaction mixture obtained in step (b) before the separation step (c); or
   (B) adding an inorganic salt to the neutralised reaction mixture obtained in step (b) before the separation step (c).

* * * * *